US012616590B2

(12) United States Patent
Pickerill et al.

(10) Patent No.: US 12,616,590 B2
(45) Date of Patent: May 5, 2026

(54) ASSISTIVE DEVICE WITH HYBRID CONTROL SYSTEMS

(71) Applicant: REHABILITATION INSTITUTE OF CHICAGO, Chicago, IL (US)

(72) Inventors: Tom Pickerill, Chicago, IL (US); James Lipsey, Chicago, IL (US)

(73) Assignee: Rehabilitation Institute of Chicago, Chicago, IL (US)

( * ) Notice: Subject to any disclaimer, the term of this patent is extended or adjusted under 35 U.S.C. 154(b) by 1004 days.

(21) Appl. No.: 17/756,368

(22) PCT Filed: Dec. 7, 2020

(86) PCT No.: PCT/US2020/063668
§ 371 (c)(1),
(2) Date: May 24, 2022

(87) PCT Pub. No.: WO2021/113847
PCT Pub. Date: Jun. 10, 2021

(65) Prior Publication Data
US 2023/0050006 A1 Feb. 16, 2023

Related U.S. Application Data

(60) Provisional application No. 62/943,913, filed on Dec. 5, 2019.

(51) Int. Cl.
*A61F 2/70* (2006.01)
*A61F 2/50* (2006.01)
(Continued)

(52) U.S. Cl.
CPC .............. *A61F 2/70* (2013.01); *A61F 2/5044* (2013.01); *A61F 2/64* (2013.01); *G16H 40/63* (2018.01);
(Continued)

(58) Field of Classification Search
CPC .. A61F 2/70; A61F 2/5044; A61F 2/64; A61F 2002/6818; A61F 2002/6863;
(Continued)

(56) References Cited

U.S. PATENT DOCUMENTS

| | | | | |
|---|---|---|---|---|
| 4,409,529 A | * | 10/1983 | Basford | .................. A61F 2/583 623/64 |
| 6,755,870 B1 | * | 6/2004 | Biedermann | ............. A61F 2/70 623/24 |

(Continued)

OTHER PUBLICATIONS

European Patent Office, Extended European Search Report, Application No. 20895951.0, September 20, 202, 6 pages.
(Continued)

*Primary Examiner* — Jerrah Edwards
*Assistant Examiner* — Maximilian Tobias Spencer
(74) *Attorney, Agent, or Firm* — Polsinelli PC

(57) ABSTRACT
An assistive device is disclosed that includes a plurality of control systems for controlling active and passive tasks. The assistive device accommodates active power generation when needed, but is otherwise configured to switch to passive control for other tasks. The assistive device further includes a continuously variable transmission to optimize movement of the assistive device for a variety of tasks. The assistive device includes a lower limb embodiment defining an artificial knee joint controlled by the plurality of control systems.

19 Claims, 16 Drawing Sheets

(51) Int. Cl.

| | |
|---|---|
| *A61F 2/64* | (2006.01) |
| *A61F 2/68* | (2006.01) |
| *A61F 2/76* | (2006.01) |
| *G16H 40/63* | (2018.01) |

(52) U.S. Cl.
    CPC ................. *A61F 2002/6818* (2013.01); *A61F 2002/6863* (2013.01); *A61F 2002/701* (2013.01); *A61F 2002/704* (2013.01); *A61F 2002/7625* (2013.01); *A61F 2002/7635* (2013.01); *A61F 2002/764* (2013.01)

(58) Field of Classification Search
    CPC .......... A61F 2002/701; A61F 2002/704; A61F 2002/7625; A61F 2002/7635; A61F 2002/764; G16H 40/63
    See application file for complete search history.

(56) References Cited

U.S. PATENT DOCUMENTS

| | | | | |
|---|---|---|---|---|
| 2006/0249315 | A1* | 11/2006 | Herr | ...................... A61F 2/6607 623/47 |
| 2008/0114272 | A1 | 5/2008 | Herr et al. | |
| 2009/0299480 | A1 | 12/2009 | Gilbert et al. | |
| 2013/0204395 | A1 | 8/2013 | Gramnaes | |
| 2015/0127118 | A1 | 5/2015 | Herr et al. | |
| 2016/0158029 | A1* | 6/2016 | Kuiken | ..................... A61F 2/64 623/24 |
| 2018/0177614 | A1* | 6/2018 | Wang | ................... A61F 2/6607 |
| 2019/0328551 | A1* | 10/2019 | Gregg | ...................... A61F 2/70 |

OTHER PUBLICATIONS

Lenzi, T. et al., "Actively Variable Transmission for Robotic Knee Prostheses," International Conference on Robotics and Automation (ICRA), May 29-Jun. 3, 2017, pp. 6665-6671.
Patent Cooperation Treaty, International Search Report and Written Opinion, International Application No. PCT/US2020/063668, date of mailing Feb. 26, 2021, 7 pages.
European Patent Office, Communication Pursuant to Article 94(3) EPC, Application No. 20895951.0, May 6, 2025, 3 pages.
European Patent Office, Extended European Search Report, Application No. 24194718.3, Nov. 20, 2024, 6 pages.

* cited by examiner

FIG. 2B

Assistive
Device
200

350

354

(A)

306

201

352

360

ASSISTIVE
DEVICE
200

224

225

226

227

228

230

229

$$\tau_{TOT}(\theta, \delta_2) = \frac{T_{knee}}{T_{mot}} = \tau(\theta, \delta_2) \cdot \frac{2\pi}{Lead} \cdot \frac{48}{18} \cdot$$

$\theta$ = Knee Joint Position $\delta_2$ = Slider Crank Moment Arm Length

FIG. 5

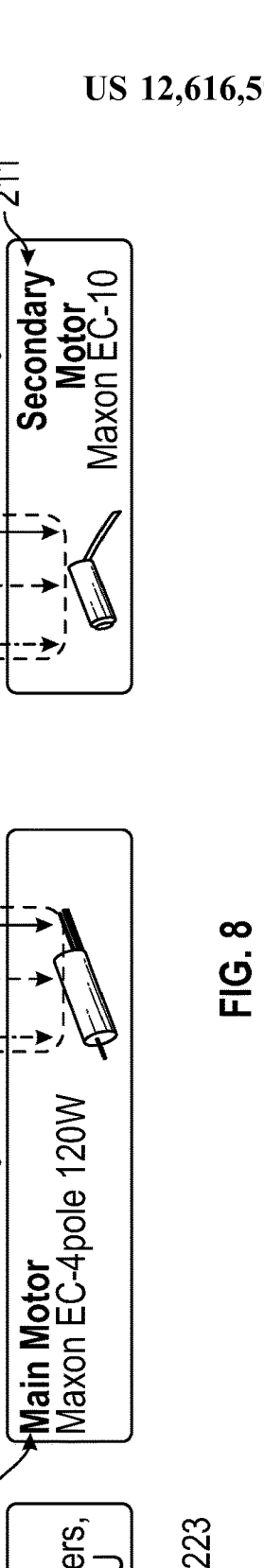

High-Level Controller
Linux Gumstix

Mid-Level Controller
Custom Micropython

Low-Level Controller
Dynamic Breaking
Drive Circuit

Main Motor
Maxon EC-4pole 120W

Sensors
Rotary Encoders,
Load Cell, IMU

Mid-Level Controller
Custom Micropytnon

Low-Level Controller
Maxon Escon
24/2

Secondary Motor
Maxon EC-10

State Machine
Ambulation Mode?
Phase?

Control Parameters

Modified PD
Controller

Desired Current

MOSFETs

Motor Winding Current

Control Parameters

PID Position
Controller

Desired Current

PID Current
Controller

Motor Winding Current 231
225
232
233
201
202,227,224,215,223

$$Output = K_p \times error + K_d \times \frac{\Delta error}{\Delta time}$$

where:

$K_p = Stiffness\ parameter$ $K_d = Damping\ parameter$

FIG. 10

$$Output = \frac{K_1}{error} + K_2 \times \frac{\Delta error}{\Delta time}$$

where:

$K_1$ = Proportional parameter $K_2$ = Derivative parameter

FIG. 11

ASSISTIVE DEVICE WITH HYBRID CONTROL SYSTEMS

CROSS REFERENCE TO RELATED APPLICATIONS

The present document is a non-provisional application that claims benefit to U.S. Provisional Application Ser. No. 62/943,913, filed on Dec. 5, 2019, which is herein incorporated by reference in its entirety.

FEDERALLY SPONSORED RESEARCH OR DEVELOPMENT

The invention was made with government support under National Institute on Disability, Independent Living, and Rehabilitation Research (NIDILRR) award nos. 90REGE0003 and 90RE5014 and National Institutes of Health (NIH) award no. 2R01HD079428. The government has certain rights in the invention.

FIELD

The present disclosure is generally directed to prosthetic and rehabilitation devices; and more specifically, to an assistive device configured for hybrid control that includes an active control system and a passive control system and is adapted to switch to either control system as needed for a given task.

BACKGROUND

With most commercially available lower limb prostheses, there is a common tradeoff between function and weight. Passive devices, which make up a majority of commercial knee prosthesis, are designed with constant or variable resistances at the joint level. They are lightweight, quiet and robust, but provide only limited function. Powered prosthetic knees on the other hand provide net positive power to assist with stairs and getting up from a seated position. However, they are inefficient during walking and standing, can be too slow for faster walking, and come at the cost of significant added weight.

There is a need for a prosthetic knee that does not compromise on function or weight, which provides power for tasks when needed, and is lightweight and small enough to be used comfortably by a wider range of amputees. It is with these observations in mind, among others, that various aspects of the present disclosure were conceived and developed.

BRIEF DESCRIPTION OF THE DRAWINGS

FIG. 2B is an illustration of a cross-sectional view of one particular embodiment of the assistive device of FIG. 2A taking the form of a lower limb assistive device.

FIG. 5 is an illustration of an equation for computing a transmission ratio calculation as referenced in the present disclosure.

FIG. 8 is an illustration of a "passive" control system overview associated with the assistive device described herein.

FIG. 10 is an illustration of a basic impedance control equation which may be implemented as described herein.

FIG. 11 is an illustration of a modified proportional derivative (PD) control equation which may be implemented as described herein.

Corresponding reference characters indicate corresponding elements among the view of the drawings. The headings used in the figures do not limit the scope of the claims.

DETAILED DESCRIPTION

Figure 1:
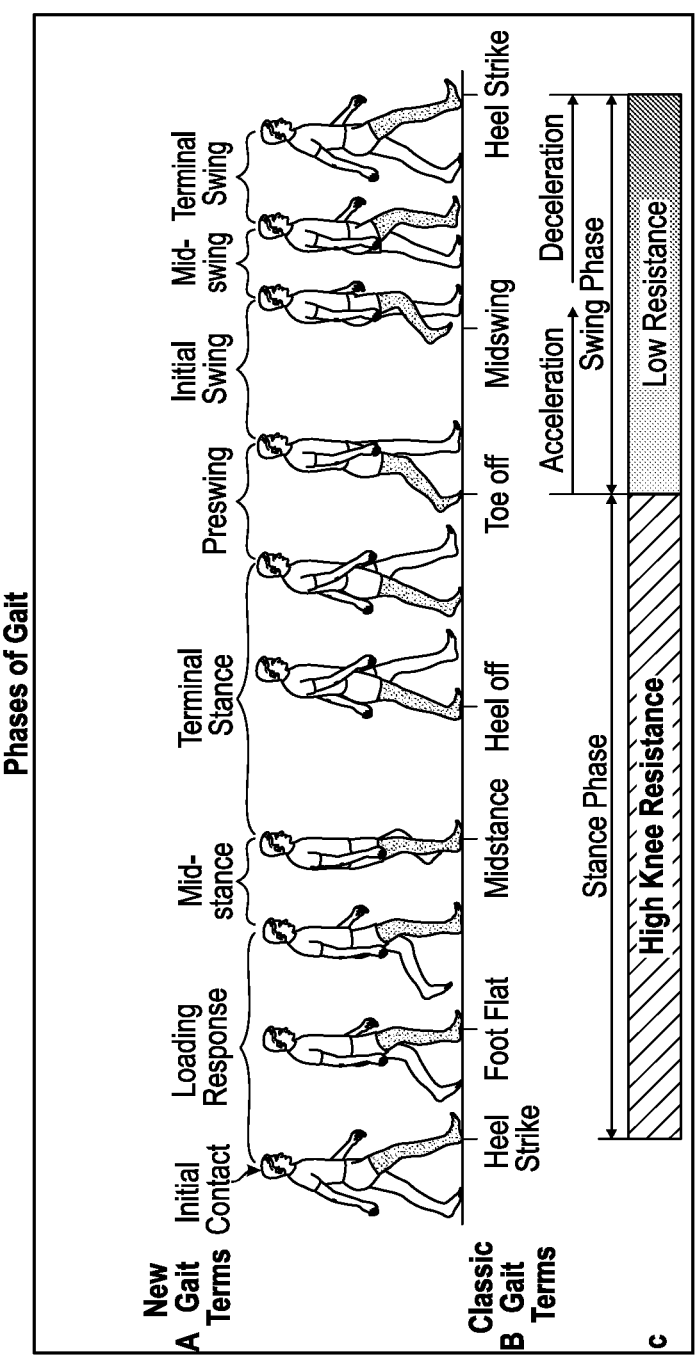
FIG. 1 is an illustration of the phases of gait as referenced in the present disclosure.

Aspects of the present disclosure relate to embodiments of an assistive device controlled by a plurality of control systems selectively engaged for active and/or passive tasks. In some embodiments, the assistive device includes a continuous variable transmission, and dynamic braking control such that the device is optimized for a wider range of tasks. The assistive device is energy efficient, yet suitable for adaptation to the task at hand. The assistive device may be embodied as a lower limb assistive device, and may include any number of actuating components for operating a knee joint (i.e., artificial joint resembling a natural knee), including both active and passive tasks, as described herein. Turning to the drawings, wherein like reference numerals refer to like elements, the present disclosure is illustrated as being implemented in a suitable environment. The following description is based on embodiments of the claims and should not be taken as limiting the claims with regard to alternative embodiments that are not explicitly described herein.

Knee Dynamics & Prosthetics Background

The human knee must generate and dissipate a range of power during different ambulation tasks and the different phases of each task (FIG. 1). For example, during level ground walking the knee must stay "locked" during stance phase to keep the knee from buckling under load. After toe-off the knee must become "loose" to allow it to flex during swing phase to provide ground clearance for the foot. As it extends, energy must be dissipated quickly and smoothly to stop the knee in the fully extended position just prior to heel contact (heel strike). On the other hand, climbing stairs requires positive power to lift the entire weight of the user up and over each step in a controlled manner.

Prosthetic knees are typically either passive, active or semi-active. Passive devices are compact devices that provide very limited function, usually only useful for level ground walking. They have a fixed static or passively varied resistance at the joint that allows for limited swing phase control, and cannot adapt to different walking speeds. Additionally, during stance phase there is a risk of buckling, as there is little resistance at the knee. Some passive knees employ a four-bar mechanism (polycentric knees) or a load activated mechanical brake to keep the leg straight during stance phase. However, these devices still require that the prosthesis alignment be shifted to ensure the weight line falls in front of the knee axis and are still prone to buckling in some situations.

Semi-active knees (or microprocessor knees) can actively vary the knee resistance to adapt to different ambulation modes and to provide better stance and swing control. For example, the Ottobock C-leg uses a hydraulic damper with valves that are adjusted via micro-controller to alter the knee resistance. Semi-active knees offer greater stability than passive knees and more natural gait dynamics than passive and active knees. They require very little electrical power to operate. However, they still require charging and they do not provide net positive power for stairs and standing up from a chair.

Active knees provide net positive power for climbing stairs and ramps and getting up from a seated position. The powered actuator controls all phases of gait. However, during walking, standing and ramp descent, the knee is mainly dissipating mechanical energy. Active knees typically dissipate energy by applying torque (current) through the motor to oppose motion, which can consume significant electrical energy. Additionally, with active devices there is often a tradeoff between torque and speed. For example, a device that is strong enough to power up stairs may be slow during walking. Conversely, a knee that is fast enough for a brisk walk may not provide as much assistance during stair climb. Finally, active devices are much heavier and larger than passive and semi-active devices and require frequent battery charging.

There is a clear need for a lightweight prosthetic lower limb device that provides the performance benefits of semi-active knees during net zero or negative energy tasks, while also providing net positive power to assist with stairs and standing up.

Assistive Device Design Overview

Figure 2A:
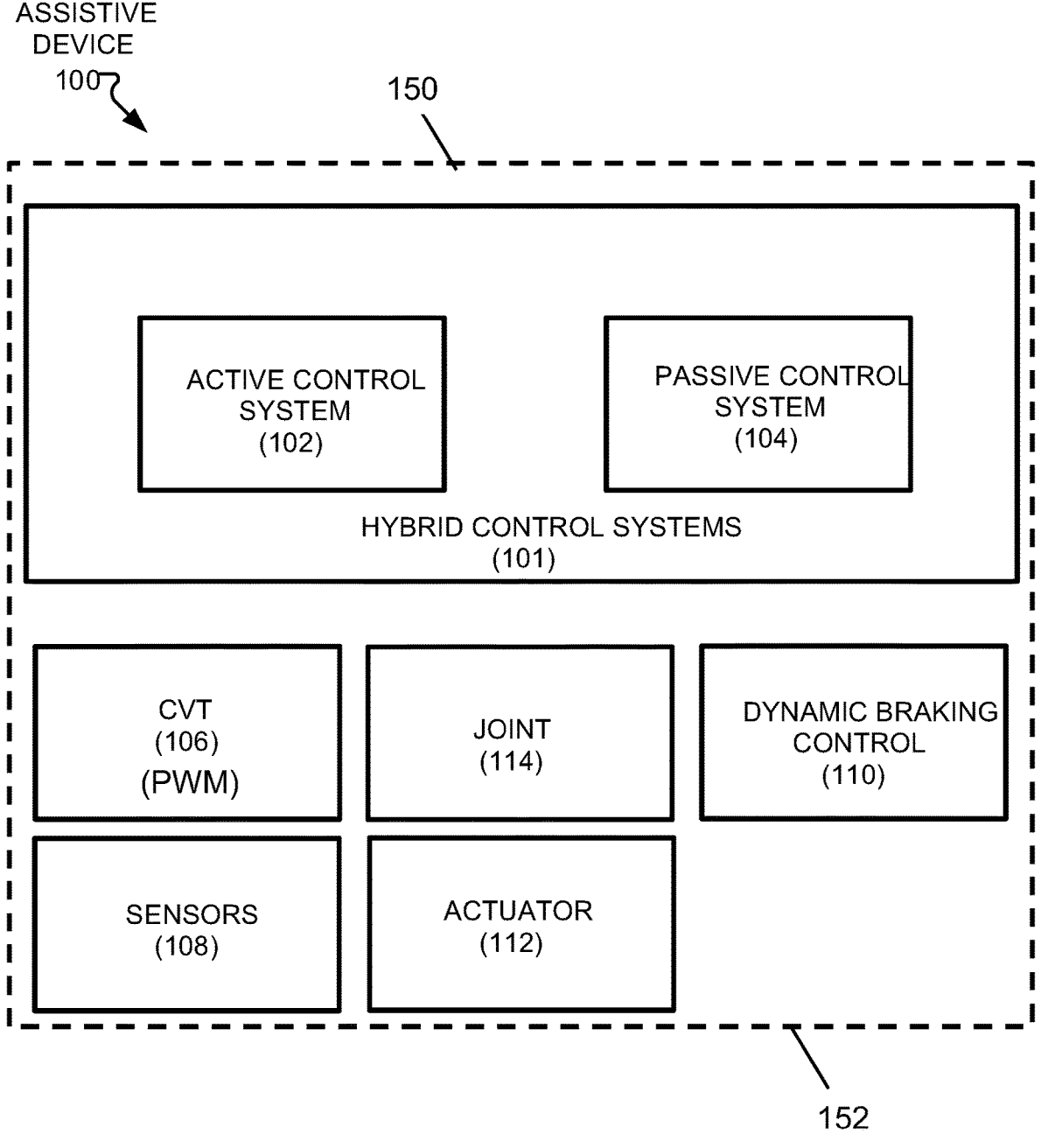
FIG. 2A is a simplified block diagram of a system including a general assistive device with hybrid passive and active control systems described herein.

Referring to FIG. 2A, a general system overview of an assistive device 100 is illustrated. With reference to U.S. Pat. No. 10,357,381 ('381 Patent), incorporated by reference in its entirety, one end (150) of the assistive device 100 may be provided with means for attaching the assistive device 100 to a residual limb of a user and may define a pyramid interface or fastener (e.g., "16" of the '381 patent) for attaching to a socket (e.g., "60" of the '381 Patent) or to an implanted component of the user. Other suitable attachment means may be utilized. The other end (152) of the assistive device 100 may be configured for attachment to a pylon and/or a foot (e.g., "90" of the '381 patent).

Figure 2B:
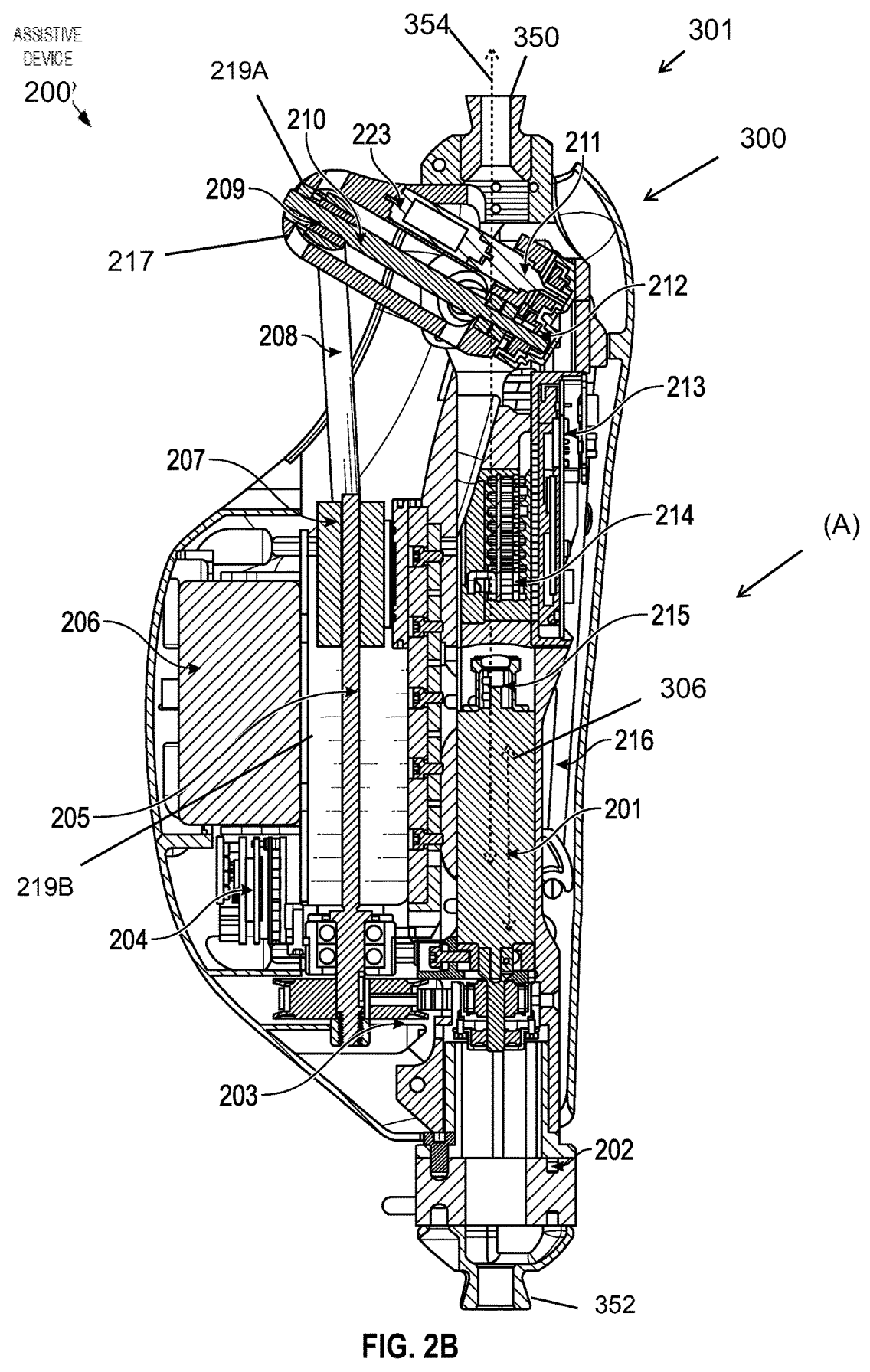

The assistive device 100 is responsive to the technical problems and drawbacks of conventional prosthetics and assistive devices described herein. For example, the assistive device 100 implements and selectively engages separate control systems (collectively hybrid control systems 101), including an active control system 102 and a passive control system 104, to control "active" and "passive" tasks, respectively. For simplification, "active" tasks refer to tasks that require net positive energy and "passive" tasks refer to net zero or negative energy tasks. In FIG. 2B described herein and in the following text, the focus mainly relates to one possible embodiment of the assistive device 100 taking the form of a lower limb prosthesis including a knee joint. However, it should be appreciated that the hybrid or dynamic nature of the hybrid control systems 101, and the features associated with the novel selective engagement of the active control system 102 and the passive control system 104 described herein may be applied for any other embodiment of the assistive device 100 configured for movement or assistance of any artificial joint; including, by non-limiting example, an artificial elbow joint, or the like. Further, the hybrid control systems 101 may be applied to an exoskeleton or a powered orthosis to augment the movement of a natural joint. As indicated in FIG. 2A, the hybrid control systems 101 can be implemented to control one or more of a mechanical actuator 112 or other mechanical and/or electromechanical components, which may be configured to facilitate movement of an artificial joint 114 (e.g., knee joint).

In general, the assistive device 100 switches between the two hybrid control systems 101 of FIG. 2A seamlessly and quickly, based on the needs for a given task. When net positive energy is needed, for instance when powering up stairs or standing from a seated position, the "active" control system 102 is engaged. However, if net zero or negative energy is needed, the "active" control system 102 is disabled and the "passive" control system 104 engaged. In some embodiments, the "passive" control system 104 functions similar to many commercial "semi-active" knees, for example Ottobock's C-Leg. The assistive device 100 does not limit a particular ambulation mode to a specific one of the hybrid control systems 101. For example, during the course of stair ascent or descent, both of the "active" control system 102 and the "passive" control system 104 can be used. While the "active" control system 102 typically consumes more electrical energy, the "passive" control system 104 consumes minimal electrical energy. Being adapted to engage the "active" control system 102 only when needed or desired, the assistive device 100 is much more efficient than fully active devices (e.g., fully active knee devices). In addition, the "passive" control system 104 can typically handle higher speeds associated with many passive tasks, such as brisk walking. Compared to active devices or active knees, when the "passive" control system 104 is used, it provides for more quiet, efficient operation and more natural joint dynamics.

In some embodiments, the "passive" control system 104 implements a form of rheostatic dynamic braking, and a novel control strategy to quickly vary the amount of power dissipated at, e.g., the joint 114 (and knee joint 300). Dynamic braking uses an electromechanical motor as a generator to convert mechanical energy into electrical energy. In rheostatic dynamic braking, the electrical energy dissipates as thermal energy through the motor windings, which resists motion of the joint. Thus, power is dissipated without consuming additional electrical power from a battery of the assistive device 100. Prosthetic knees are good candidates for rheostatic dynamic braking, as heavy braking is needed only periodically, and thus there is no risk of overheating the motor windings.

Another key feature of the assistive device 100 is that embodiments of the assistive device 100 include a continuously variable transmission (CVT) 106 defined by the mechanical actuator 112 or one or more actuating components. The CVT 106 is used to adjust the mechanical transmission ratio to optimize the mechanical power profile of the joint for "active" and "passive" tasks. By example, the dynamics of a human knee require speeds and torques that are hard to replicate with an electro-mechanical motor alone. A mechanical transmission is typically required to produce useful dynamics at the knee joint of a lower limb prosthetic. A mechanical transmission uses mechanical advantage to reduce or amplify the speed and torque. The amount of reduction and amplification is defined by the transmission's speed or gear-ratio. Typical mechanical transmissions have a static speed-ratio, and any amplification of torque for example corresponds to an inversely proportional reduction in speed. A variable transmission, on the other hand, allows the ratio to be adjusted. The CVT 106 when implemented by the assistive device 100 allows the assistive device 100 to provide the needed 120 Nm of peak torque needed for stair climbing and standing from a seated position. Ordinarily, at the same speed-ratio, lower limb embodiments of the assistive device 100 would be too slow for low-torque, high-speed knee tasks such as level ground walking. By using the CVT 106, the ratio can be optimized to provide the needed speed and torque required for each task of the human knee.

Mechanical System Overview

Lower Limb Embodiment of the Assistive Device (100) Including a Knee Joint

Figure 2C:
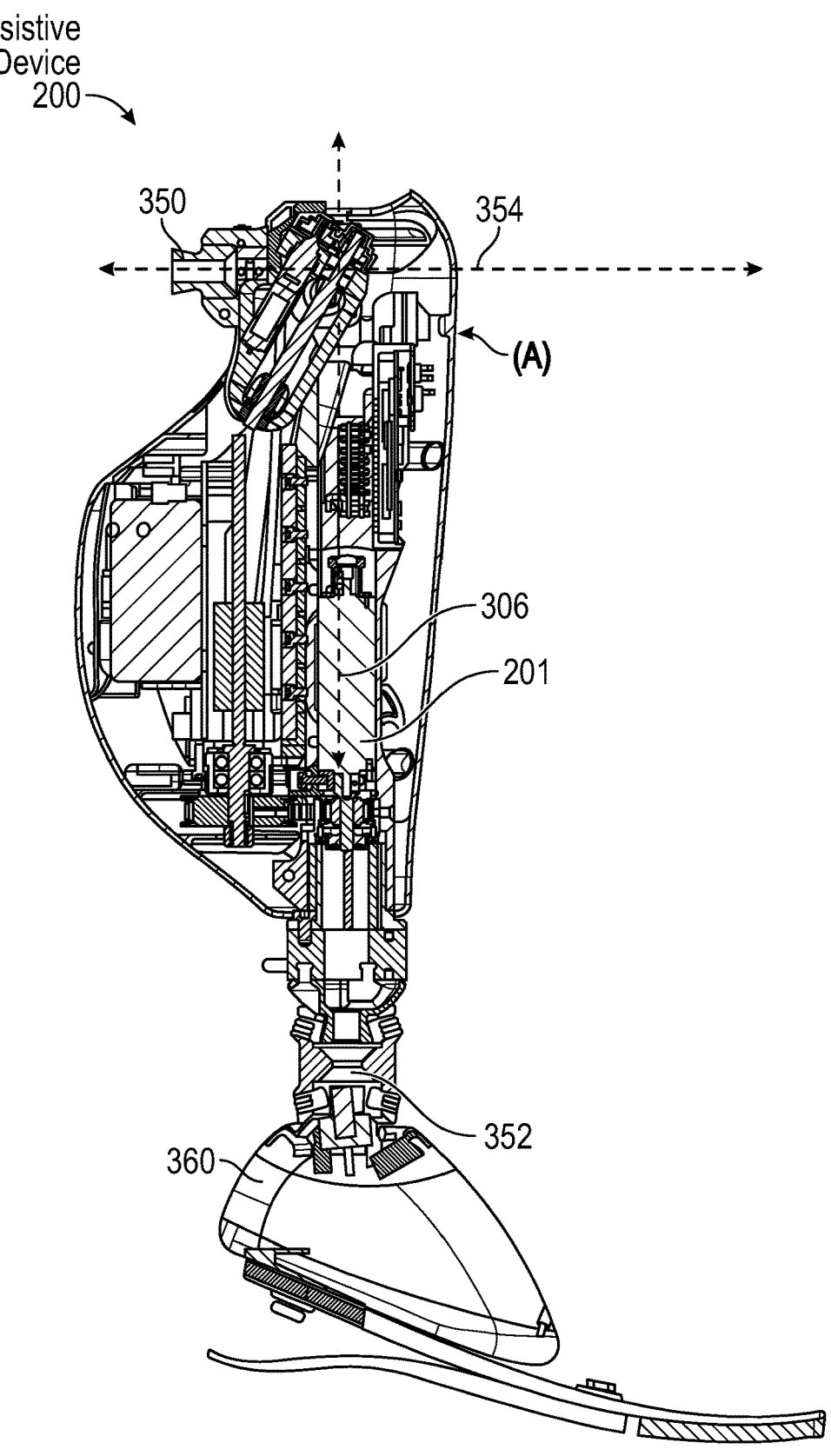
FIG. 2C is an illustration of a cross sectional view of the embodiment of FIG. 2B demonstrating a change in knee joint angle.
Figure 3:
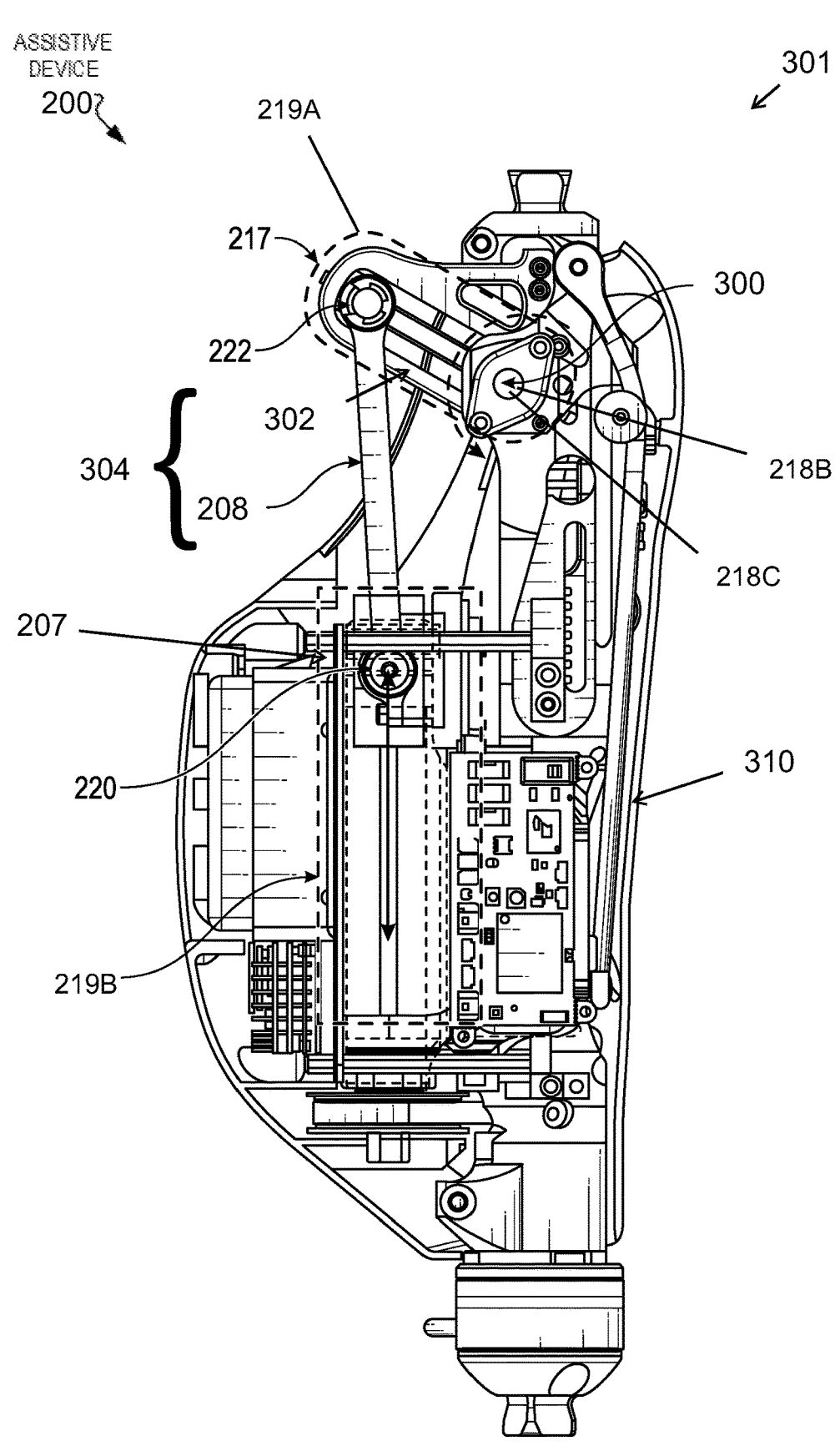
FIG. 3 is another illustration of a cross-sectional view of the lower limb assistive device of FIG. 2B highlighting a slider crank mechanism.

Referring to FIGS. 2B, 2C, and FIG. 3, a lower limb embodiment of the assistive device 100 is shown, designated lower limb device 200 and defining a knee joint 300. The lower limb device 200 may define a prosthetic or an orthosis for movement/motion assistance. The lower limb device 200 may generally be implemented, for example, for a user that is entirely devoid of a natural knee and lower limb such as shown in FIGS. 3-6 of the '381 patent referenced herein or alternately in the manner shown in FIG. 28 of the '381 patent. A first end 350 of the lower limb device 200 may be provided with means for attachment of the lower limb device 200 to a residual limb of a user and may define a pyramid interface or fastener (e.g., "16" of the '381 patent) for attaching to a socket (e.g., "60" of the '381 Patent) or to an implanted component of the user. Other suitable attachment means may be utilized. A second end 352 of the lower limb device 200 may be configured for attachment to a pylon and/or a foot (e.g., "90" of the '381 patent, and shown as "360" in FIG. 2C).

The lower limb assistive device 200 includes one or more actuating components 301 (mechanical and/or electro-mechanical) for actuating or otherwise engaging the knee joint 300 and other aspects of the lower limb assistive device 200 including a brushless DC motor 201 (e.g., Maxon Motor EC-4pole 24V, 120 W) which converts electrical to mechanical energy in the form of rotational motion. The rotational motion is transmitted to a roller screw 205 (e.g., Rollvis, pitch diameter 4.5 mm, lead 2 mm) through a timing belt transmission 203. The roller screw 205 converts the rotational motion to linear motion, and a slider crank 217, including a first portion 219A of the slider crank 217 and a second portion 219B, converts the linear motion back to rotational motion at the knee joint 300. The slider crank 217 includes a connecting rod 208, which is pinned to a roller screw nut 207 at a first rod pivot 220. The other end of the connecting rod 208 is pinned to the slider crank 217 at a second rod pivot 222. The roller screw nut 207 transmits linear motion through the connecting rod 208 to the second rod pivot 222, which rotates the slider crank 217 around the crank pivot 218B or the knee axis 218C. Further details of this actuation system can be found in the '381 patent herein incorporated by reference, specifically, the "four-bar linkage" system disclosed therein and shown for example in FIGS. 14A and 14B.

CVT Mechanism (106)

Figure 6:
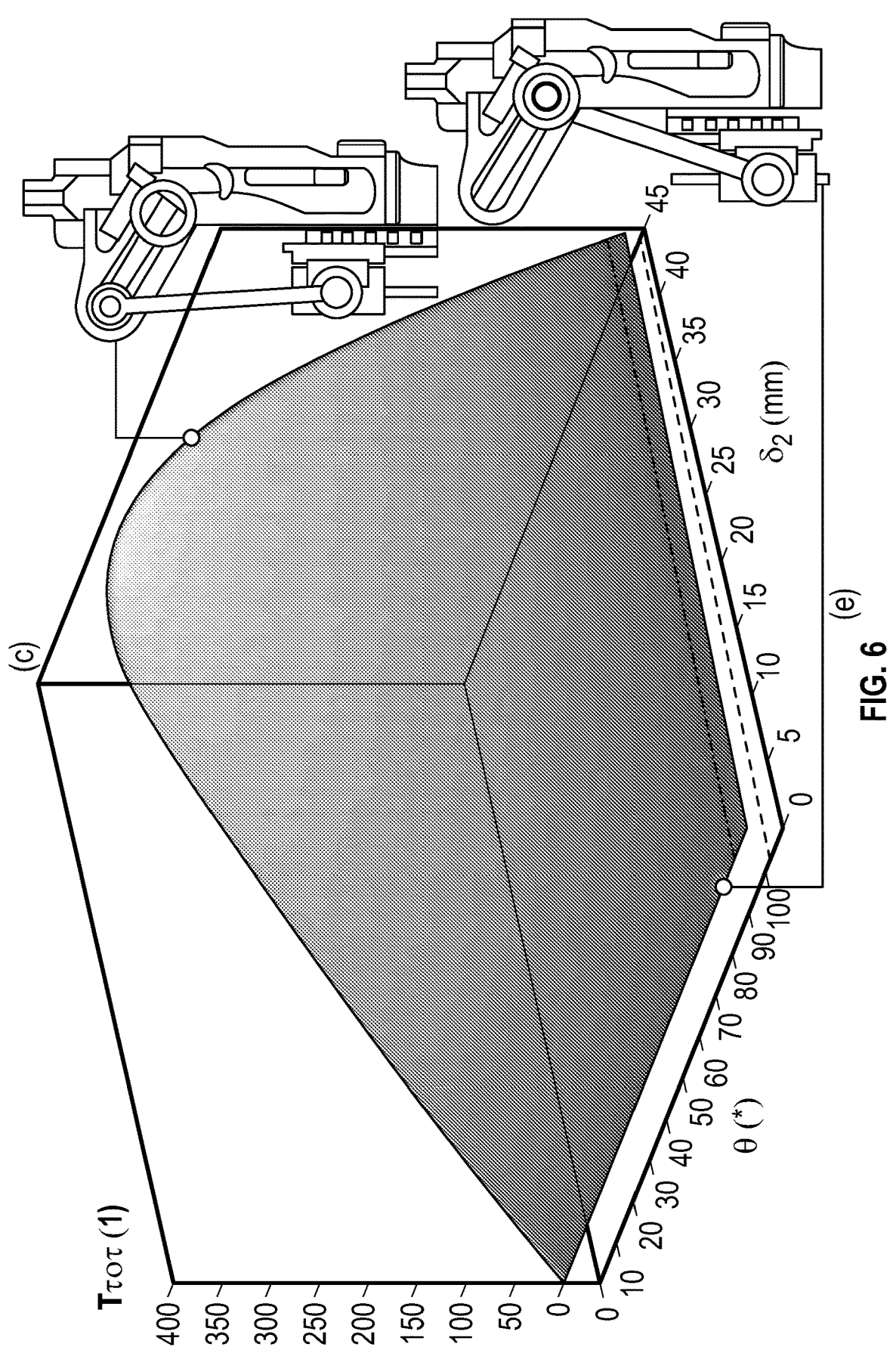
FIG. 6 is an illustration of a three-dimensional (3D) graph demonstrating transmission ratio vs. crank moment arm length and knee joint position as referenced in the present disclosure.

Referring to FIG. 2B and FIG. 3 and further illustrated in FIG. 6, the CVT 106 mechanism, defined by the one or more actuating components 301, modifies the transmission ratio of the slider crank 217 by changing the distance 302 between the second rod pivot 222 and the crank pivot 218B on the first portion 219A of the slider crank 217. A second brushless DC motor 211 (e.g., Maxon Motor EC22 24V) is connected through a spur gear transmission 212 to a linear ACME screw 210, which produces linear motion at the lead screw nut 209. The lead screw nut 209 is connected to the second rod pivot 222. Linear motion at the lead screw nut 209 changes the length 304 of the slider crank 217 moment arm, by changing the distance (304) between the second rod pivot 222 and the crank pivot 218B. Further details of the CVT mechanism 106 can be found in the '381 patent herein incorporated by reference. The total speed ratio of the lower limb device 200 is a function of both the slider crank 217 moment arm length and the knee joint 300 position (see change/movement of knee joint 300 position shown in FIG. 6). The total transmission ratio from the axis 306 of symmetry that runs through the center of the motor 201 to the knee axis 218C can be found using Equation 1, shown in FIG. 5.

Sensors

Figure 4:
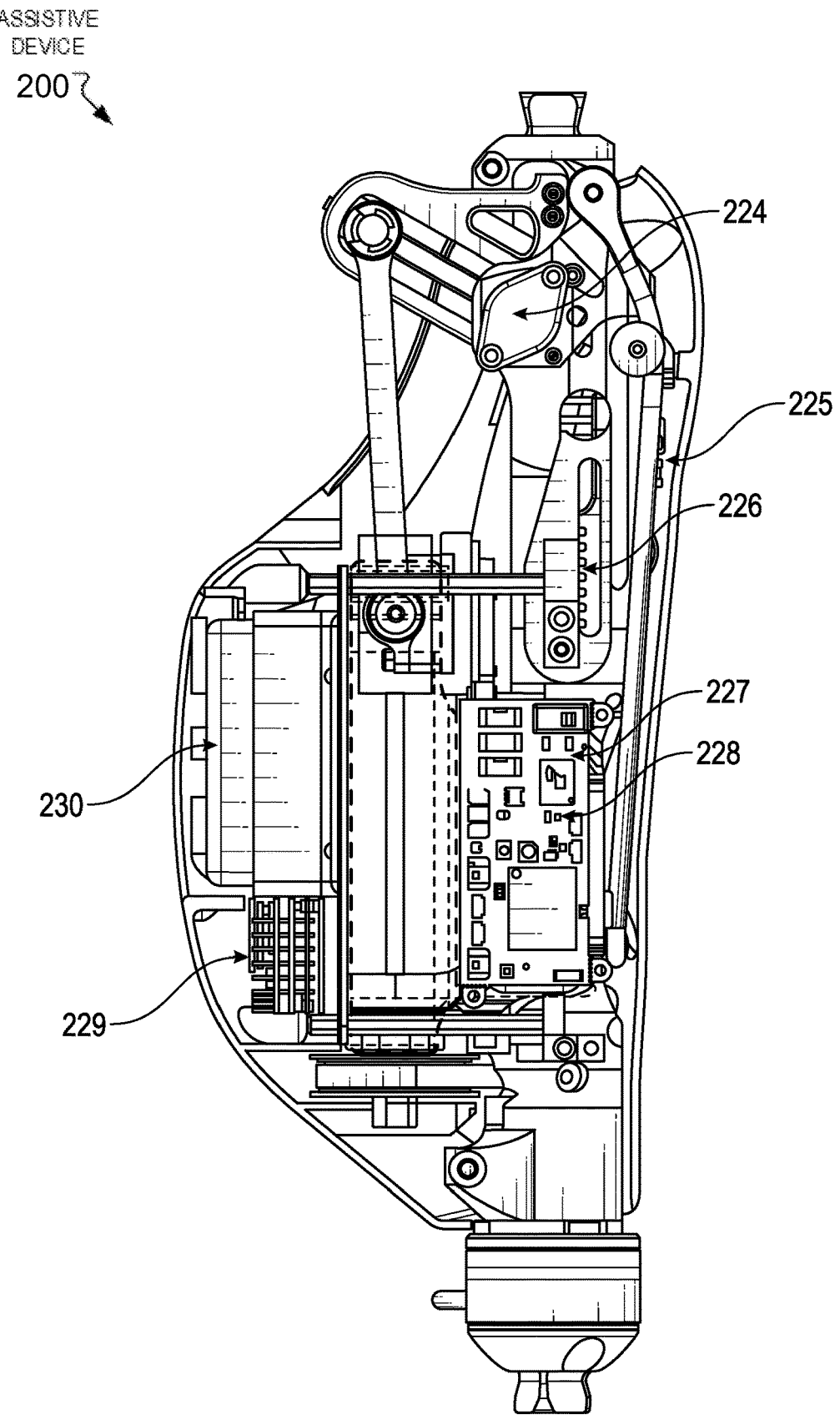
FIG. 4 is another illustration of a cross-sectional view of the lower limb assistive device of FIG. 2B highlighting possible electronics hardware.

The hybrid control systems 101 described herein may be implemented to control aspects of the lower limb assistive device 200 (and may be implemented fully on board the lower limb assistive device 200, partially on-board the lower limb assistive device 200, or totally off-board and in communication with the lower limb assistive device 200 via any wired or wireless communication form). In some embodiments, feedback from the lower limb assistive device 200 is provided to the hybrid control systems 101 using an array of electro-mechanical sensors, designated sensors 108 in FIG. 2A and sensors (202, 227, 224, 215, 223) in FIG. 8. For example, the lower limb device 200 may include a Hall-based absolute encoder 224 positioned at the knee axis 218C to measure a knee joint angle (A). In general, the knee joint angle (A) is defined at the intersection between the longitudinal axis 306 of the motor 201, and a longitudinal axis 354 of the first end 350; noting that the first end 350 is ordinarily fixed to a residual limb or socket. In a standing or extended position as shown in FIGS. 2B, 3, and 4, the knee joint angle (A) is approximately zero degrees (longitudinal axis 306 and longitudinal axis 354 generally extend in parallel and do not intersect). On the other hand, in a bent or seated configuration shown in FIG. 2C, the knee joint angle (A) of the lower limb assistive device 200 is approximately ninety degrees due to a shift in position of the first end 350 relative to the motor 201 that results in the intersection shown between the longitudinal axis 306 and the longitudinal axis 354 (at about a 90 degree angle).

In addition, the lower limb device 200 may include a Hall-based incremental encoder 215 attached to the main DC motor 201 to measure motor position, and a second Hall-based incremental encoder 223 attached to the secondary DC motor 211 to measure the slider crank 217 moment arm length 304. Further still, the lower limb device 200 may include a six axis load cell 202 (e.g., Sunrise Instruments M3713D) positioned as shown in FIG. 2B to measure ground level reaction forces and moments. In addition, an Inertial Measurement Unit (IMU) 227 (e.g., TDK MPU-9250) may be used to measure knee acceleration and inclination angles.

Figure 7:
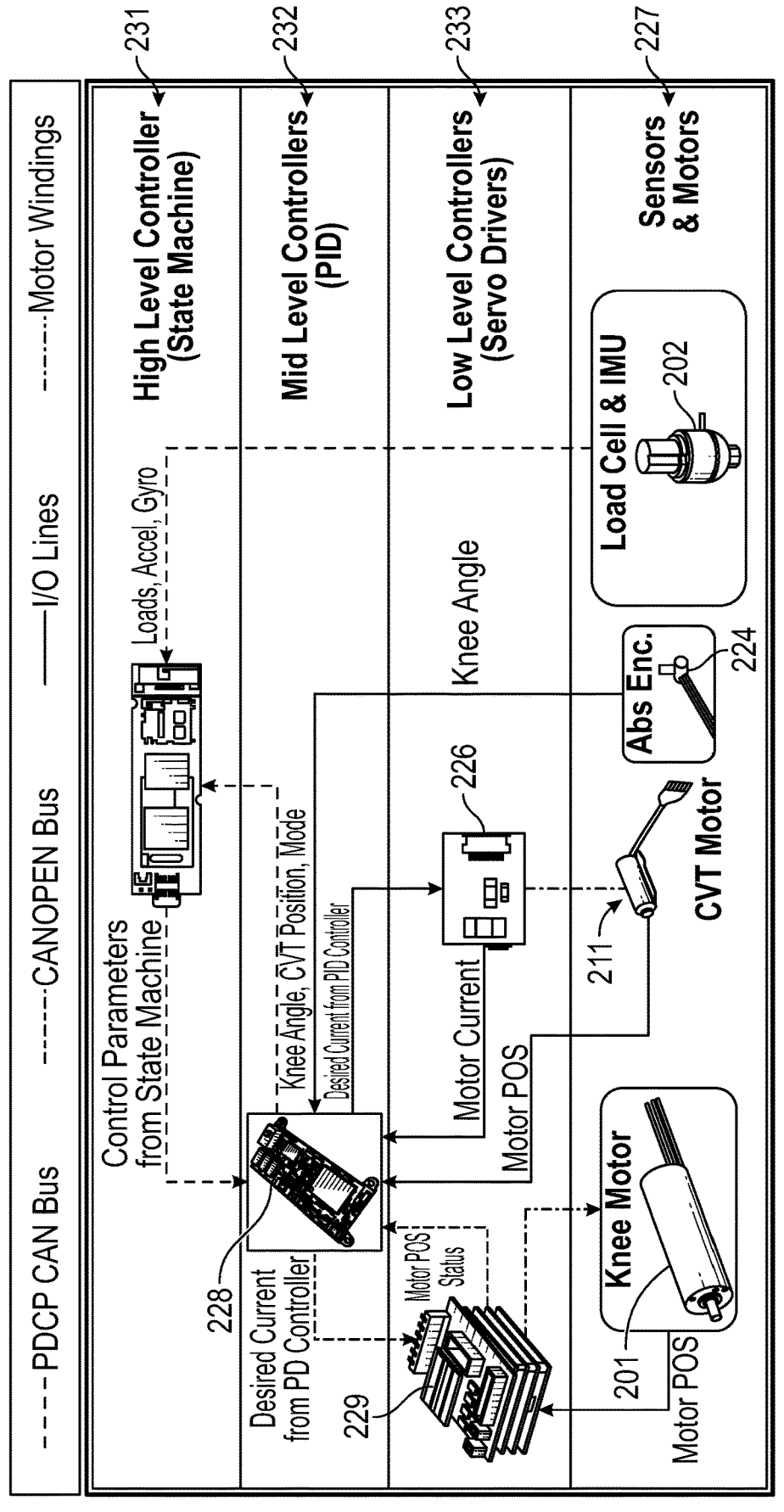
FIG. 7 is an illustration of an overview for control system hardware of the assistive device described herein.
Figure 9:
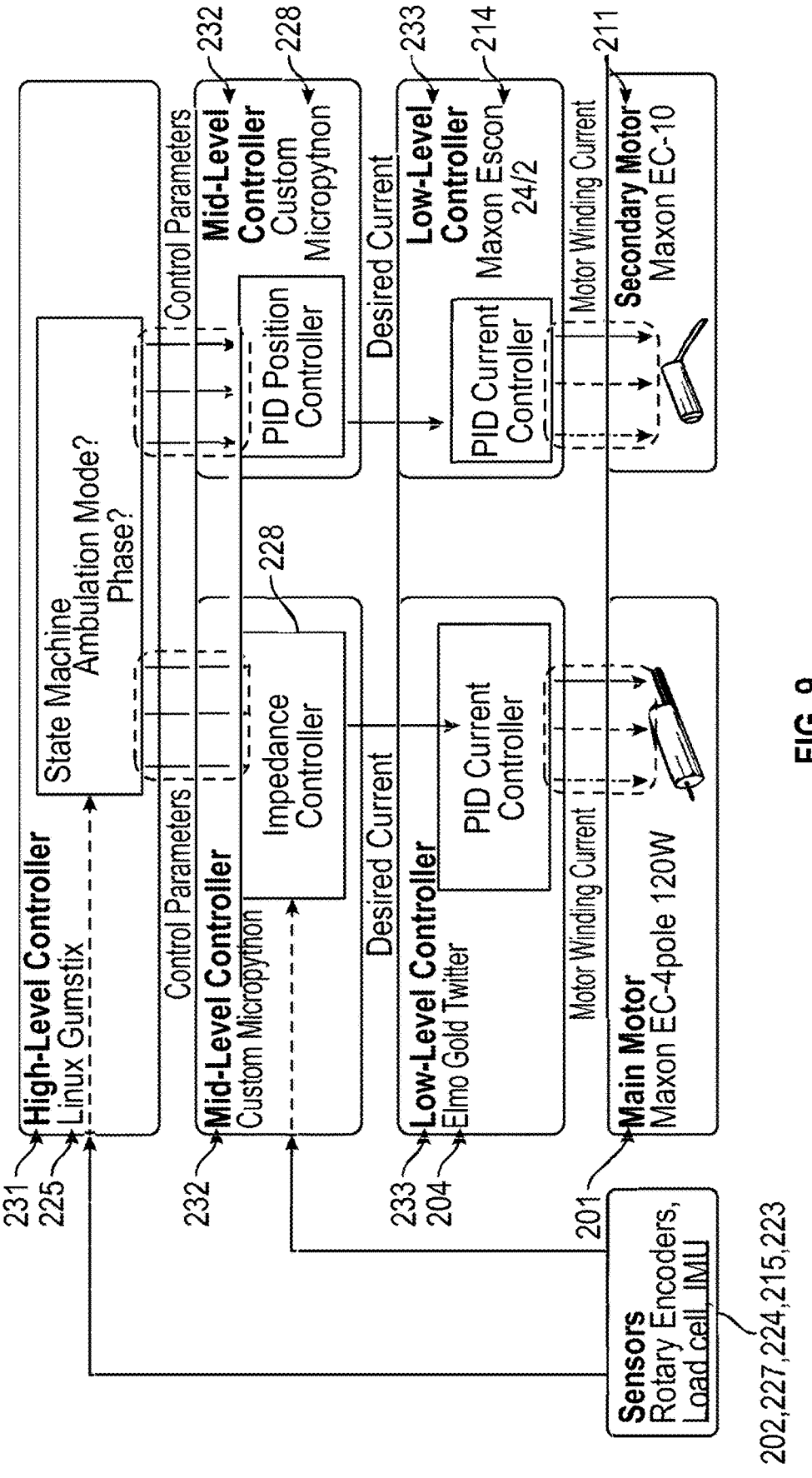
FIG. 9 is an illustration of an "active" control system overview associated with the assistive device described herein.

System Control Overview (FIGS. 7, 8, 9)

In some embodiments, the control of the lower limb device 200 may be driven by three tiers of controllers; specifically, one or more of a high-level controller 231, a mid-level controller 232, and a low-level controller 233; and each tier of controllers may respectively include an "active" controller and a "passive" controller. The high-level controller 231 control may be implemented on a Linux based computer-on-module 225 (e.g., Gumstix Overo Air) which runs a state machine that analyzes sensor feedback data from the lower limb device 200 and determines a proper state of the knee joint 300 and lower limb assistive device 200. As shown in FIG. 7, sensor feedback data received by high level controller 231 includes load, acceleration, and gyroscopic data as determined by load cell 202 and IMU 227, and high level controller 231 determines a state of the knee lower limb device 200 based on the sensor feedback data. For instance, the state machine determines if the lower limb device 200 is in the stance or free swing phase of walking (shown in FIG. 1), based on ground reaction forces detected by the load cell 202, as well as the position of the lower limb device 200 and a shank inclination angle detected by the IMU 227. The state machine also must distinguish between different modes of ambulation (i.e. stair ascent, level ground walking, ramp descent, etc.). Based on the determined state of the knee joint 300, the high-level controller 231 sends specific control parameters to the mid-level controller 232 to control active operations and passive operations of the lower limb device 200 such as desired currents applied to motors 201 and 211

The mid-level controller/s 232 as described above may include an "active" controller (FIG. 9) and "passive" controller (FIG. 8). The mid-level controllers 232 may be run on a custom printed circuit board (PCB) 228 with, e.g., an ESP32 based microcontroller, such as a Pycom Wipy 2.0, running Micropython. The mid-level controllers 232 may include an "active" controller (FIG. 9) including an impedance controller, which accepts control parameters including desired knee angle, stiffness and dampening as inputs from the high-level controller 231. Impedance controller of the mid-level controllers 232 calculate a desired motor current based on control parameters received from the high level controller 231, which is subsequently communicated to the low-level controller 233 (FIG. 10) for direct control of main motor 201. The "passive" controller (FIG. 8) of the mid-level controllers 232 uses a modified PD control approach, which accepts a desired knee angle and two braking factors as inputs from the high-level controller 231 (FIG. 11). The mid-level controller 232 calculates the desired motor braking of the lower limb device 200, which is discussed in more detail in the following paragraphs ("Dynamic Braking Control"). The lower limb assistive device 200 further includes one or more of a battery 310, which may be positioned along the PCB 228 as shown and in electrical communication with the same.

The lower limb device 200 may include a commercial servo driver 229 (e.g., Elmo Gold Twitter G-TWI 30/60SE). Servo driver 229 is the "active" controller of the low-level controllers 233. The motor windings of main motor 201 are connected directly to the servo driver 229, and the DC motor 201 can be controlled by modulating the current drawn through the motor windings, which is directly related to motor torque output. Low-level controller 233 receives a desired motor current from the midlevel controller 232. The low-level controller 233 uses its own PD control approach to set the actual motor current output based on the desired motor current received from the midlevel controller 232.

Dynamic Braking Control

Background

As discussed above, dynamic braking is the use of an electric motor to convert mechanical energy of a rotating shaft into electrical and thermal energy. This is typically accomplished by connecting winding phases of a motor to a common ground. The motor then acts as a generator. Turning the motor shaft generates electrical energy and a temporary resistance to a change in current, creating a back electromotive force (back EMF). The back EMF acts to resist motor shaft rotation, effectively braking the motor. In rheostatic dynamic braking, the electrical energy generated is dissipated as heat inside of the motor. Regenerative dynamic braking is an alternative method that returns the energy to a battery, but requires more complex electronics and is more expensive than rheostatic dynamic braking.

Dynamic braking is a well-known method for braking electro motors. Many commercial servo drivers offer the ability to enable a dynamic brake to stop a motor. However, with most available systems, the amount of braking cannot be varied, and the brake is either fully ON or fully OFF.

It is possible to control the amount of dynamic braking by varying the strength of the magnetic field in the motor windings. This can be accomplished by changing the total resistance through the windings connected to a common ground. This could be achieved by using a variable resistor or potentiometer, however this has limitations. Variable resistors are typically adjusted manually by turning a dial, which is impractical for automated control. Another option is a digital potentiometer, which is an integrated circuit that mimics the function of a potentiometer and is controlled digitally. However, digital potentiometer resistance values are typically too high and power ratings too low for use for adequate dynamic braking. The current through a resistor is equal to the voltage across the resistor divided by the resistance value. The amount of current through the resistor is directly proportional to the braking torque, and so the motor braking torque is increased by minimizing the braking resistor's resistance value. Additionally, increased braking increases the amount of electrical power dissipated through the braking circuit. In order to handle sufficient braking, a braking resistor must minimize resistance and maximize its power rating.

Assistive Device Braking Control Method

In some embodiments, the assistive device 100, including the embodiment of the lower limb device 200, uses an alternative method for controlling the amount of dynamic braking, designated dynamic braking control 110 in FIG. 2A. Instead of varying the physical resistance value between the windings and the common ground, the current through the windings of main motor 201 is varied using Pulse Width Modulation (PWM). Each winding phase of main motor 201 is connected to a switching transistor that couples and decouples the winding phase to and from a common ground. This varies the total current through the windings. The transistors are switched ON and OFF at very high frequencies using a digital signal. Two level PWM is a digital signal that has two states: high and low (ON and OFF). Two parameters control a PWM signal: frequency and duty cycle. The frequency is the rate of state change cycles per second in Hertz (Hz). Duty cycle is the amount of time the signal stays ON during each cycle. Duty cycle is typically expressed as a percentage of one cycle. For example, a duty cycle of 30% and frequency of 1 Hz describes a signal that cycles once every second, or one second per cycle. For each cycle, the signal stays ON for 0.3 s and OFF for 0.7 s (FIG. 11).

Figure 12:
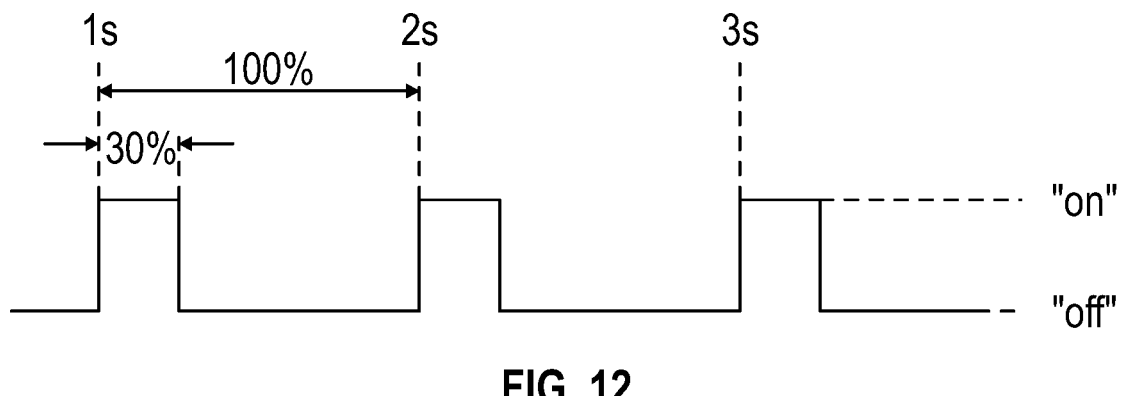
FIG. 12 is an illustration of a pulse width modulation duty cycle as referenced herein.
Figures 13A, 13B:
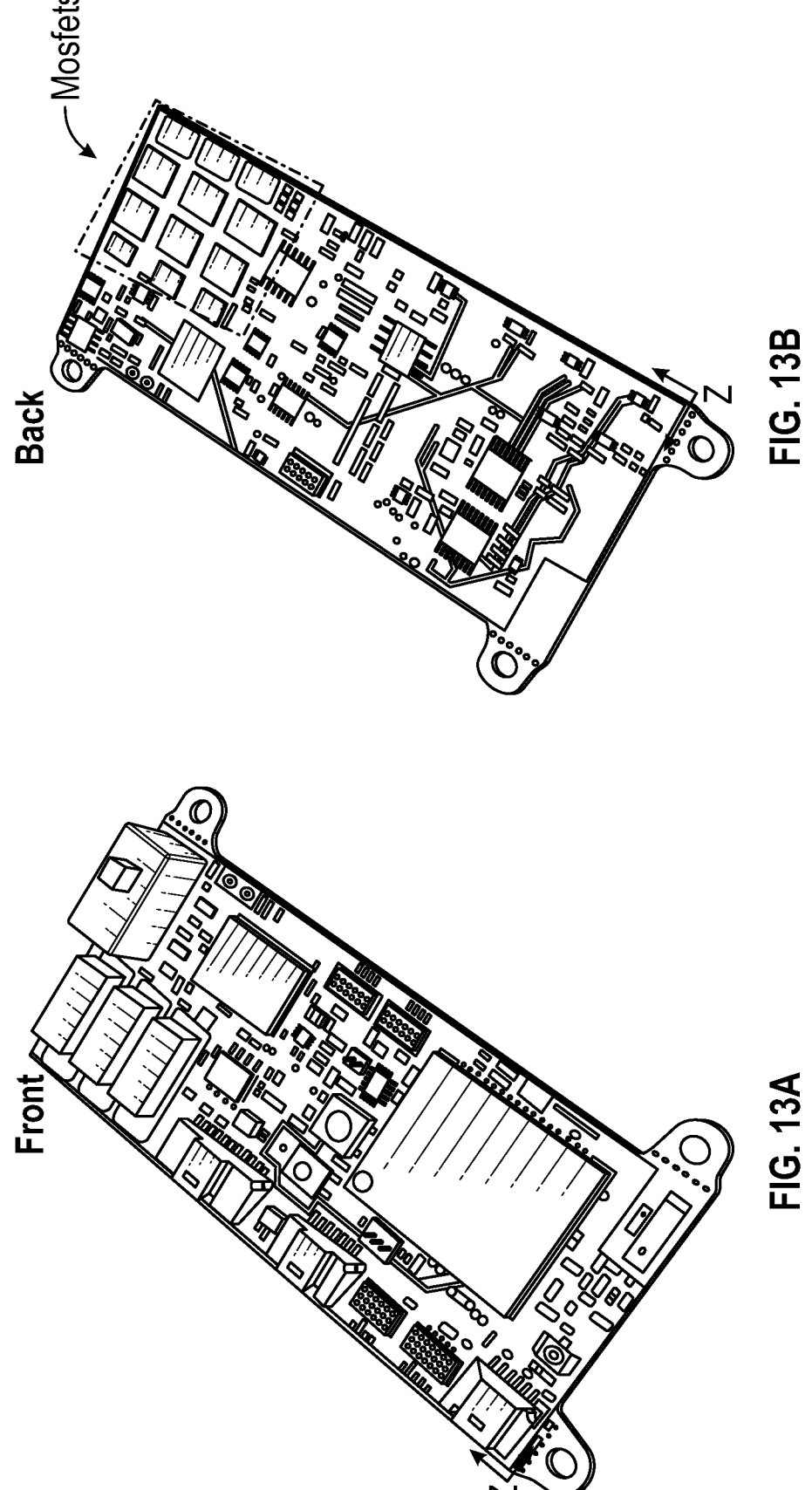
FIGS. 13A-13B are front and back view respectively of a custom control PCB for dynamic braking control as referenced herein.

In some embodiments, the lower limb device 200 uses a three-phase brushless motor. This requires three switching transistors to short each winding phase of the three winding phases to common ground for dynamic braking. Two main types of transistors are contemplated: enhancement and depletion mode MOSFETs. Enhancement mode MOSFETs have the advantage of lower "on state" resistances, smaller sizes, as well as wider availability. However, enhancement mode MOSFETs default to the OFF state at zero gate-source voltage. Depletion mode MOSFETs typically have higher on state resistance, have limited availability, but default to an ON state at zero gate-source voltage. In some embodiments, the lower limb device 200 uses two separate sets of MOS-FETs to control braking (FIG. 12). When the lower limb device 200 is powered ON, the "passive" mid-level controller 232 uses a low-resistance enhancement mode MOSFET to modulate braking. When the lower limb device 200 is powered OFF, for example when the battery 310 is drained, the enhancement mode MOSFETs open and the depletion mode MOSFETs close, shorting/coupling the winding phases of main motor 201 to ground. This allows for static braking of the assistive device 200 even when unpowered. This is important in order to keep the assistive device 200 from becoming completely loose, which can help to prevent knee buckling or falls. Since in the OFF state, braking requirements are not as high, the higher resistance depletion mode MOSFET provides sufficient braking. In addition, it is possible to change a static resistance value that the device 200 defaults to in the OFF state by using an additional removable or variable resistor. The depletion mode transistor is used solely to provide braking at the device 200 when power is lost. When the lower limb device 200 is powered ON, whether in active or passive mode, the depletion mode is always open. When power is lost, the depletion mode transistor closes, shorting/coupling the (winding phases) of main motor 201 to ground. The enhancement mode transistor is pulsed with the PWM signal to vary an amount of braking in passive mode. In active mode, the enhancement mode transistor is always open.

The mid-level "passive" controller 232 uses a PWM signal with a frequency of 70,000 Hz. The mid-level controller 232 modulates the duty cycle with an update frequency of up to 400 Hz. This allows for very responsive control of the amount of braking, as well as full stance and swing phase control, as well as stair descent resistance can be achieved using this method. For example, during stance phase, the PWM duty cycle can be set to 100%, for maximum knee resistance to keep the knee "locked". After toe-off, the PWM duty cycle is immediately reduced to lower the knee resistance and allow it to smoothly flex during swing phase. Dynamic braking control using PWM requires only the power required for the microcontroller 232.

Figure 14:
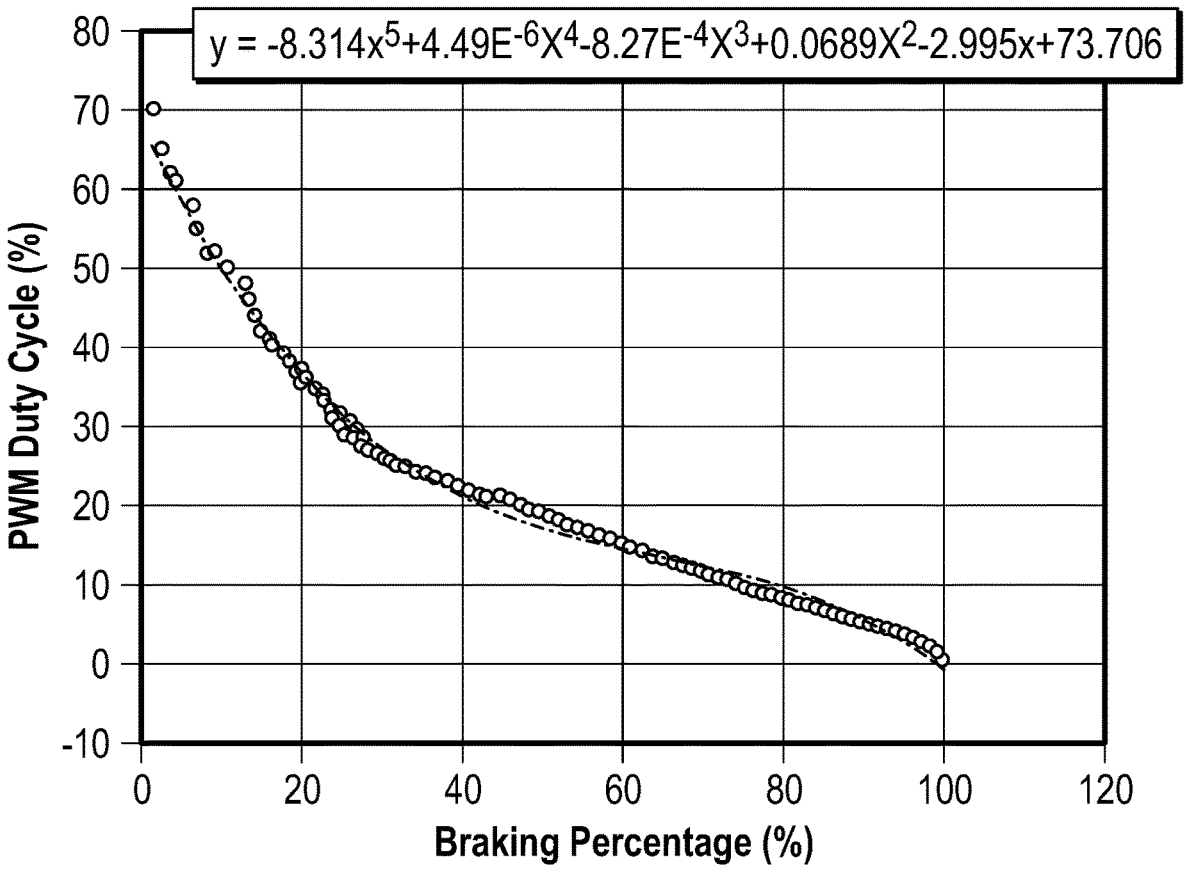
FIG. 14 is a graph illustrating $5^{th}$ order polynomial fit for duty cycle v. braking percentage.

Through experimental testing it was determined that the relationship between PWM duty cycle and the amount of braking is non-linear for this system. Braking values were measured experimentally, and the relationship between duty cycle and braking was fit to a $5^{th}$ order polynomial (FIG. 14). In order to reduce the computational requirements on the Micropython controller 232, the polynomial equation was used to generate a lookup table. The lookup table maps the output of the mid-level controller 232 in terms of desired braking percentage to a duty cycle value. The PWM signal is transmitted to the gate of the braking MOSFETs which in turn modulate the knee braking output.

In order to switch between "passive" and "active" control, the mid-level controller opens and closes the enhancement mode MOSFETs accordingly. The three motor winding phases of motor 201 are connected to the MOSFETs, as well as the servo driver terminals. When the MOSFETs are closed, the winding phases are coupled/shorted directly to a common ground. When the MOSFETs are open, the motor winding phases pass directly to the servo driver 229 terminals for control of the motor 201. The mid-level controller 232 includes logic that opens the MOSFETs and enables the servo driver 229 when "active" control is needed. On the other hand, the mid-level controller 232 disables the servo driver 229 and closes the MOSFETs when "passive" control is needed. For additional safety, the gate of each MOSFET is tied to a Safe Torque Off (STO) of the servo driver 229. STO is a basic driver safety feature that acts as a safe stop. Digital logic inputs enable and disable the STO. When STO logic is low, the servo driver 229 is disabled. Connecting the logic for the enhancement and depletion MOSFET gates to the servo driver's STO lines significantly reduces the likelihood of shorting the motor winding phases to ground while the servo driver 229 is active.

In addition to PWM, the CVT 106 also can control the amount of knee resistance. By simultaneously adjusting the CVT 106 and PWM, the knee speed, knee resistance and the electrical power dissipation profile can be optimized for different ambulation modes and users. For example, for descending stairs, increasing the CVT gear ratio allows for increased support of the user as the knee joint 300 flexes. Reducing the CVT gear ratio can increase the output knee speed for fast walking. With the ability to control the mechanical transmission ratio with the CVT 106 and amount of dynamic braking with PWM control, the assistive device can optimize performance for a wide operating range, providing increased efficiency and functionality to the user.

Overview

The assistive device uses separate control systems to control "active" and "passive" tasks. Additionally, by combining this with a CVT mechanism 106, the present device 200 can be optimized for a wide range of tasks. Prosthetic knees, including active knees, mainly perform energy dissipating tasks such as standing, walking and descending stairs and ramps. However, many users could benefit from the ability to produce net positive power at the knee joint for tasks such as stair climbing and standing from the seated position. This is especially true for the elderly population. However, existing prosthetic knee devices that produce net positive power are very heavy and can be too slow for many tasks. The assistive device allows for "active" power generation when needed, but otherwise switches to "passive" control. Since the "passive" control consumes significantly less electrical power, the total knee operation is much more efficient that a fully active device.

In sum, with passive mode tasks, e.g. level ground walking, the knee swings freely at a high speed. In a fully active device, the motor must generate this motion rather than the natural gait cycle. Thus, power is consumed for every step and as a result, a much larger, heavier battery is needed for a fully-active system. Additionally, a fully active system must be able to generate high torque at slower speeds (such as climbing stairs or standing up). This requires a larger performance envelope, as the fully active system must accommodate both high-speed, low torque operations (e.g. swing phase during walking), and lower-speed, high torque operations. Doing so requires either a compromise in efficiency by operating the motor substantially outside where it is tuned for optimal efficiency, or adding weight in the form of a more complicated transmission, which can also impose power losses. The present design of the lower limb assistive device 200 allows the system to minimize weight and efficiency by optimizing the active mode actuation system for high-torque, low speed operation.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. An assistive device with hybrid control systems, comprising:
a knee joint;
one or more actuating components for actuating the knee joint;
a plurality of sensors positioned along the one or more actuating components that provide feedback data associated with the knee joint;
a hybrid control system defined along the knee joint and in operable communication with the plurality of sensors, including:
an active control system that provides net positive energy, and
a passive control system that varies power dissipated at the knee joint to accommodate net zero or negative energy;
a variable transmission mechanism defined by the one or more actuating components that adjusts a mechanical transmission ratio to optimize a mechanical power profile of the knee joint for predetermined active and passive tasks;
a dynamic braking control mechanism configured for varying an amount of braking of the one or more actuating components in real time, comprising:
a plurality of transistor pairs for braking control, each of the plurality of transistor pairs including an enhancement mode transistor and a depletion mode transistor, the plurality of transistor pairs engageable for unique braking conditions, and
a pulse wave associated with the passive control system defining a duty cycle adjustable by the processing device to provide responsive control of the amount of braking; and
a processing device in operable communication with the plurality of sensors and the hybrid control system, the processing device configured to determine a state of the knee joint based on the feedback data and engage either or both of the active control system or the passive control system based on the state of the knee joint.

2. The assistive device of claim 1, wherein, based on a change in the state of the knee joint, the processing device is configured to engage the active control system to perform a first set of mechanical functions, and the processing device is configured to disengage the active control system and is configured to engage the passive control system to perform a second set of mechanical functions to minimize consumption of electrical energy.

3. The assistive device of claim 1, wherein the passive control system utilizes rheostatic dynamic braking to dissipate electrical energy as thermal energy through windings of a motor of the one or more actuating components which resists motion of the knee joint.

4. The assistive device of claim 1, wherein the active control system utilizes impedance control, which includes acceptance of a desired knee joint angle, stiffness and dampening as inputs from the processing device to calculate a desired motor current.

5. The assistive device of claim 1, wherein the passive control system accepts a desired knee joint angle and two braking factors as inputs from the processing device to calculate a desired braking parameter for a motor of the one or more actuating components.

6. The assistive device of claim 1, wherein the one or more actuating components comprises:
a first motor for converting electrical energy to mechanical energy as rotational motion;
a roller screw that receives and converts the rotational motion from the first motor to linear motion; and
a slider crank assembly that converts the linear motion back to rotational motion at the knee joint, including:
a crank, and
a connecting rod, including a first end engaged to a nut of the roller screw at a first rod pivot, and a second end of the connecting rod engaged to the crank at a second rod pivot, the nut of the roller screw transmitting the linear motion through the connecting rod to the second rod pivot to rotate the crank about an axis.

7. The assistive device of claim 6, wherein the variable transmission mechanism modified a transmission ratio of the slider crank assembly by changing a distance between the first rod pivot and the second rod pivot based on the state of the knee joint which accommodates speed and torque specifications of the one or more actuating components predetermined to be suitable for the state of the knee joint.

8. The assistive device of claim 6, wherein the plurality of sensors includes encoders for measuring knee joint angle position and a first motor position to measure a crank moment arm length.

9. The assistive device of claim 1, wherein the plurality of sensors includes a load cell that measures ground level reaction forces and moments, and an inertial measurement unit (IMU) that measures knee joint acceleration and inclination angles.

10. The assistive device of claim 1, wherein the pulse wave is transmitted to a gate of the plurality of transistor pairs which in turn modulates a knee joint braking output.

11. The assistive device of claim 10, wherein each transistor of the plurality of transistor pairs couples an electromagnetic coil of a first motor with a ground voltage line.

12. The assistive device of claim 11, wherein the first motor is configured to prevent rotating when a high logic level is applied to the plurality of transistor pairs and wherein net positive power is applied to the first motor when a low logic level is applied to the enhancement mode transistors.

13. The assistive device of claim 12, wherein the enhancement mode transistor closes when a high logic level of the pulse wave is applied to the gate of each enhancement mode transistor thereby grounding each of the electromagnetic coils and generating a back electromagnetic force preventing rotation of the first motor.

14. The assistive device of claim 12, wherein the enhancement mode transistor is configured to open when a low logic level of the pulse wave is applied to the gate of each enhancement mode transistor thereby enabling a signal from the active control system to control the rotation of the first motor.

15. The assistive device of claim 12, wherein the depletion mode transistor is configured to open when power is supplied to the assistive device.

16. The assistive device of claim 12, wherein the depletion mode transistor is configured to close when power is not supplied to the assistive device, thereby grounding each of the electromagnetic coils and generating a back electromagnetic force preventing rotation of the first motor.

17. The assistive device of claim 16, wherein an impedance between the depletion mode transistor and the electromagnetic coils is configured for preselection in order to vary a strength of the back electromagnetic force preventing rotation of the first motor when power is not applied to the assistive device.

18. A system for substituting a joint of the human body, comprising:

an assistive device including a joint, one or more actuating components for engaging the joint, and a plurality of sensors;

a hybrid control system for controlling the assistive device, including:

an active control system that provides net positive energy, and a passive control system that varies power dissipated at the joint to accommodate net zero or negative energy, and a variable transmission mechanism defined by the one or more actuating components that adjusts a mechanical transmission ratio to optimize a mechanical power profile of the one or more actuating components for predetermined active and passive tasks;

a dynamic braking control mechanism configured for varying an amount of braking of the one or more actuating components in real time, comprising:

a plurality of transistor pairs for braking control, each of the plurality of transistor pairs including an enhancement mode transistor and a depletion mode transistor, the plurality of transistor pairs engageable for unique braking conditions, and a pulse wave associated with the passive control system defining a duty cycle adjustable by the processing device to provide responsive control of the amount of braking;

and a processing device in operable communication with the plurality of sensors and the hybrid control system, the processing device configured to determine a state of the joint and engage either or both of the active control system or the passive control system.

19. A method of manufacturing an assistive device, comprising:

forming an assistive device including one or more actuating components and a plurality of sensors; and forming a hybrid control system that receives data from the plurality of sensors and includes a processing element for controlling the assistive device, including:

forming an active control system that provides net positive energy, forming a passive control system that varies power dissipated at a joint to accommodate net zero or negative energy, and forming a dynamic braking control mechanism configured for varying an amount of braking of the one or more actuating components in real time, comprising:

a plurality of transistor pairs for braking control, each of the plurality of transistor pairs including an enhancement mode transistor and a depletion mode transistor, the plurality of transistor pairs engageable for unique braking conditions, and a pulse wave associated with the passive control system defining a duty cycle adjustable by the processing device to provide responsive control of the amount of braking, wherein the processing element is configured to determine a state of the joint and engage either or both of the active control system or the passive control system.

\* \* \* \* \*